US011751951B2

United States Patent
Zheng et al.

(10) Patent No.: US 11,751,951 B2
(45) Date of Patent: Sep. 12, 2023

(54) SURFACE TRACKING-BASED SURGICAL ROBOT SYSTEM FOR DRILLING OPERATION AND CONTROL METHOD

(71) Applicant: Tsinghua University, Beijing (CN)

(72) Inventors: Gangtie Zheng, Beijing (CN); Shijie Zhu, Beijing (CN); Zhe Zhao, Beijing (CN); Yongwei Pan, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 432 days.

(21) Appl. No.: 17/039,881

(22) Filed: Sep. 30, 2020

(65) Prior Publication Data
US 2022/0031398 A1 Feb. 3, 2022

(30) Foreign Application Priority Data
Jul. 31, 2020 (CN) .......................... 202010756597.8

(51) Int. Cl.
*A61B 34/20* (2016.01)
*A61B 34/35* (2016.01)
(Continued)

(52) U.S. Cl.
CPC .......... *A61B 34/20* (2016.02); *A61B 17/1615* (2013.01); *A61B 17/17* (2013.01);
(Continued)

(58) Field of Classification Search
CPC ..... A61B 34/20; A61B 17/1615; A61B 17/17; A61B 34/25; A61B 34/35;
(Continued)

(56) References Cited

U.S. PATENT DOCUMENTS 6,725,080 B2 * 4/2004 Melkent ............... A61B 6/5235
606/130
8,394,114 B2 3/2013 Schaller et al.
(Continued)

OTHER PUBLICATIONS

Khan, A.. et al. "Next-Generation Robotic Spine Surgery: First Report on Feasibility, Safety, and Learning Curve," Operative neurosurgery (Hagerstown, Md.), 2019, vol. 17, No. 1, pp. 61-69.
(Continued)

*Primary Examiner* — Julian W Woo
(74) *Attorney, Agent, or Firm* — LOZA & LOZA, LLP; Michael F. Fedrick (57) ABSTRACT

A surface tracking-based surgical robot system for drilling operations includes surface scanning equipment, a robot arm, and a workstation. To perform a drilling operation, surface information for the target surgery area and the surgical tool held by the robot arm is simultaneously collected with the same surface scanning equipment. A preoperative 3D image of a surgical area and a CAD model of the surgical tool are registered to the collected surface information, through which the relative position between a surgical path and the surgical tool is obtained. Using this relative position, the robot arm aligns to the predefined surgical path using a feedback control method running on a workstation. The drilling operation is then autonomously executed by the robot arm or manually performed under the guidance of the surgical tool held by the robot arm.

11 Claims, 9 Drawing Sheets

(51) Int. Cl.
  *A61B 34/37* (2016.01)
  *A61B 34/00* (2016.01)
  *A61B 17/16* (2006.01)
  *A61B 17/17* (2006.01)
  *A61B 90/00* (2016.01)

(52) U.S. Cl.
  CPC .............. *A61B 34/25* (2016.02); *A61B 34/35* (2016.02); *A61B 34/37* (2016.02); *A61B 90/37* (2016.02); *A61B 2034/2046* (2016.02); *A61B 2090/374* (2016.02); *A61B 2090/3762* (2016.02)

(58) Field of Classification Search
  CPC ............ A61B 2034/2046; A61B 34/30; A61B 17/1604; A61B 17/164; A61B 17/1671; A61B 17/1703; A61B 17/1757
  See application file for complete search history.

(56) References Cited

U.S. PATENT DOCUMENTS

| | | | |
|---|---|---|---|
| 8,992,580 B2 | 3/2015 | Bar et al. | |
| 9,498,231 B2 | 11/2016 | Haider et al. | |
| 9,872,733 B2 | 1/2018 | Shoham et al. | |
| 9,974,613 B2 | 5/2018 | Kang et al. | |
| 9,993,305 B2* | 6/2018 | Andersson | A61B 17/1757 |
| 10,028,788 B2 | 7/2018 | Kang | |
| 10,217,277 B2 | 2/2019 | Robert et al. | |
| 11,576,685 B2* | 2/2023 | Card | A61B 17/1703 |

OTHER PUBLICATIONS

Lefranc, M. et al. "Evaluation of the ROSA Spine robot for minimally invasive surgical procedures", Expert Review of Medical Devices, 2016, vol. 13, No. 10, pp. 899-906.

Shamir, RR et al. "Surface-based facial scan registration in neuronavigation procedures: a clinical study", J Neurosurg, 2009, 111(6):1201-1206.

Jiang L. et al. "A robust automated markerless registration framework for neurosurgery navigation", Int J Med Robot, 2015,11(4):436-447.

Li, S. et al. "Experimental study of three dimensional navigahon assisted spinal surgery by multi-segment registration technology based on structured Hght scanning", National Medical Journal of China, 2011, 91(9):634 638.

Feng, B. et al. "Experiment study of three dimensional navigation assisted spinal surgery using structured light scanning", Chinese Journal of Orthopedics, 2011, 31(5):530-534.

Zhu, Shijie et al. "Markerless robotic pedicle screw placement based on structured light tracking", International Journal of Computer Assisted Radiology and Surgery (2020), https://doi.org/10.1007/s11548-020-02215-x, 14 pgs.

Mellado, N. et al. "SUPER 4PCS: Fast Global Pointcloud Registration," EUROGRAPHICS 2014 (The 35th Annual Conference of the European Association for Computer Graphics), The Eurographics Association and John Wiley & Sons Ltd. eds., vol. 33 (2014), No. 5.

* cited by examiner

SURFACE TRACKING-BASED SURGICAL ROBOT SYSTEM FOR DRILLING OPERATION AND CONTROL METHOD

FIELD OF THE INVENTION

The present invention relates to the field of surgical robots, especially for drilling operations based on surface tracking.

BACKGROUND OF THE INVENTION

Precise drilling operation is a common requirement for orthopedic surgeries, such as pedicle screw placement for spinal surgeries. The accuracy of the drilling, including the entry point and the direction, directly influences the outcome of the surgery and improper drilling may cause a catastrophic result. To improve the accuracy of the drilling operation, robot and computer technology have been used in related clinical applications in recent years and many commercial products such as surgical navigation systems and surgical robots are now available.

Currently, most navigation systems or surgical robots for drilling tasks rely on optical positioning equipment, including systems described in U.S. Pat. Nos. 9,498,231, 8,992,580, 8,394,114, 9,974,613, and U.S. Ser. No. 10/028,788; the Mazor X system (A. Khan, J. E. Meyers, I. Siasios, and J. Pollina, "Next-Generation Robotic Spine Surgery: First Report on Feasibility, Safety, and Learning Curve," *Operative neurosurgery* (Hagerstown, Md.), vol. 17, no. 1, pp. 61-69, 2019 Jul. 1, 2019); and the ROSA™ Spine system (M. Lefranc, and J. Peltier, "Evaluation of the ROSA Spine robot for minimally invasive surgical procedures," *Expert Review of Medical Devices*, vol. 13, no. 10, pp. 899-906, October, 2016). In these systems, the positions of the surgical path and the surgical tool are acquired by tracking optical markers mounted on the engaged surgical components (such as the bone, the robot arm, the image acquisition equipment, etc.) with the optical positioning system.

Although the foregoing optical positioning-based systems can achieve fairly high accuracy, there are drawbacks. Firstly, installation and registration of the optical markers make the surgery workflow more complicated and time-consuming Secondly, the positions of the surgical target and the surgical tool are indirectly tracked through a long coordinate transformation chain established via the optical markers. The errors from optical tracking, marker shifting and registration will accumulate along this transformation chain and can be difficult to perceive or compensate for.

To avoid using an optical positioning system, one solution is to rigidly connect the robot positioning system to the surgery subject. As described in U.S. Pat. No. 9,872,733, a very compact and small positioning robot can be fixed to the bone, so that even if the bone moves unexpectedly, the relative position between the bone and the robot is maintained unchanged. However, in this solution the mounting procedure of the robot is complicated. In addition, any looseness of the robot can also result in poor accuracy, and this looseness cannot be detected by the system itself.

Object tracking via surface registration has also been used in surgical robots. With 3D surface information, the position and orientation of the object with respect to the scanning equipment can be directly determined by registering the surface of an object to the scanned surface without using extra markers. This technology has primarily been used in surgical robots for neurosurgery and maxillofacial surgery (Shamir R R, Freiman M, Joskowicz L, Spektor S, Shoshan Y (2009) Surface-based facial scan registration in neuro-navigation procedures: a clinical study, J Neurosurg 111 (6):1201-1206; Jiang L, Zhang S, Yang J, Zhuang X, Zhang L, Gu L (2015) A robust automated markerless registration framework for neurosurgery navigation. Int J Med Robot 11 (4):436-447), as well as in a few in spine surgeries (Li S, Qiu G, Feng B, Cai S, Sheng L, Zhai J, Liang J (2011) Experimental study of three dimensional navigation assisted spinal surgery by multi-segment registration technology based on structured Hght scanning, National Medical Journal of China 91 (9):634-638; Feng B, Qiu G, Li S, Zheng H, Li P, Cai S, Liang J, Sheng L (2011) Experiment study of three dimensional navigation assisted spinal surgery using structured light scanning Chinese Journal of Orthopedics 31 (5):530-534). All current systems however continue to rely on optical positioning equipment, and in these systems surface tracking technology is only applied to patient tracking, and not to surgical tool tracking. In another words, the problems of traditional optical positioning-based methods, including the complexity of surgery workflow and the imperceptibility of the positioning error have not been solved by using current surface registration techniques.

SUMMARY OF THE INVENTION

The present system and method relate to the use of surgical robots to perform drilling operations based on surface tracking without the use of markers or an optical positioning system. The surface tracking-based surgical robot system for performing drilling operations can include for example a robot arm, a surgical tool, a surface scanner, and a workstation. The robot arm has a proximal end, a distal end, at least three translational degrees of freedom, and at least two rotational degrees of freedom. The surface scanner is capable of acquiring scanned data comprising surface geometry and color information of a surgery site, and can be any of a laser scanner, a ToF (time-of-flight) camera, or a structured light camera/scanner, for example. The workstation is in communication with the surface scanner and the robot arm, such as via a wired or wireless network, and is used to process the scanned data, plan a drilling path, and control motion of the robot arm.

The surgical tool of the system has a proximal end attached to the distal end of the robot arm and tool is either a surgical drill or a drill guide. If the tool is a surgical drill, the drill will have a drill head comprising a cylindrical portion between a proximal end and a distal end of the drill head and a non-cylindrical component at the distal end of the drill head. If the tool is a drill guide, the drill guide will have a cylindrical sleeve between a proximal end and a distal end of the drill guide and will also comprise a non-cylindrical component at the distal end of the drill guide. A drill bit can be secured to the distal end of the drill guide or to the distal end of the drill head. In the surgical tool, the non-cylindrical component can be any of a distally flaring-shaped component, one or more circumferential grooves, and/or one or more circumferential ridges. If the non-cylindrical component has a distally flaring-shape, the shape is preferably conical, frustoconical, hemispherical, or bell-shaped. At least a portion of an outer surface of the drill guide or the drill head preferably comprises a matte color and/or a color which is different than the color of the surgery site.

The method for performing a drilling operation on a subject involves first providing a surface tracking-based surgical robot system, which can comprise a surface scanner, a workstation, and a surgical robot having a robot arm with a surgical tool such as a surgical drill or a drill guide attached to the distal end of the robot arm. 3D image data (for example point clouds, triangular facets or meshes) of a target surgery area is acquired, such as with a CT or MRI machine, and a surgical path is then planned on this 3D image data. Surface geometry of the target surgery area is also extracted from the 3D image data to produce surface geometry data. The surface geometry data is preferably preprocessed, such as by down-sampling the data and removing a portion of the data corresponding to areas of the target surgery area which cannot be viewed from the surface scanner.

The surface scanner is then positioned so that the target surgery area can be viewed by the surface scanner, and the robot arm is likewise positioned so that the drill guide can be viewed by the surface scanner. The target surgery area is selected by creating a contour of the target surgery area from color 3D image data obtained from the scanner using a graphical user interface of the workstation and registering the robot arm to the surface scanner. The surgical tool is preferably segmented from the color 3D image data, for example using binarization and morphologic operations. Surface data corresponding to the segmented area is then segmented, and such segmented surface data is registered to a CAD model of the surgical tool to acquire a transformation from the CAD model of the surgical tool to the surgical tool. The position and direction of the surgical tool with respect to the surface scanner can then be calculated.

Registering the robot arm to the surface scanner can be performed by recording the initial direction of the surgical tool tracked by the surface scanner and calculating the direction of the surgical tool with respect to a base coordinate frame of a robot arm coordinate frame using kinematic data obtained from the robot arm. The surgical tool is then pointed to a second direction, recording the direction of the surgical tool tracked by the surface scanner and also calculating the direction of the surgical tool with respect to the base coordinate frame of the robot arm using the kinematic data obtained from the robot arm. The rotation matrix is then calculated from the base coordinate frame of the robot arm to a coordinate frame of the surface scanner according to the directions in both coordinate frames acquired in the previous two steps using a singular value decomposition method. The singular value decomposition equation used in the singular value decomposition method can be the following:

$$R_{robot}^{scan} = \underset{R \in \text{Rotation matrix}}{\arg\min} \sum_{i=1,2} \| R(n_{robot}^{tool})_i - (n_{robot}^{tool})_i \|$$

where R is a rotation matrix, $R_{robot}^{scan}$, is the rotation matrix from a base coordinate frame of the robot arm to a coordinate frame of the surface scanning equipment, $n_{robot}^{tool}$ is a direction of the distal end of the surgical drill obtained using kinematic data obtained from the robot arm, and $n_{scan}^{tool}$ is a direction of the distal end of the surgical drill obtained from image data from the scanner.

After the robot arm is registered to the surface scanner, a robot movement quantity is calculated using a feedback control method according to a relative spatial relationship between the surgical path and the surgical tool, with the robot movement quantity comprising a translational component and a rotational component. This step is repeated until an alignment error between the surgical tool and the surgical path is below a preset threshold, thereby aligning the surgical tool to the surgical path. The robot movement quantity comprises a translation direction component ("$d_{robot}$") and a rotation component ("$r_{robot}$") of a tip of the surgical tool in the base coordinate frame of the robot arm ("$C_{robot}$"). The translation direction component $d_{robot}$ can be expressed as:

$$d_{robot} = (R_{robot}^{scan})^T e_{trans},$$

in which $R_{robot}^{scan}$ is a rotation matrix from the coordinate frame of the surface scanner ("$C_{scan}$"), and $e_{trans}$ indicates a translational error quantity. The rotation component $r_{robot}$ can be expressed as:

$$r_{robot} = (R_{robot}^{scan})^T e_{rot},$$

with $e_{rot}$ indicating a rotational error quantity.

The translational error quantity of the robot movement quantity can be determined by the following formula:

$$e_{trans} = d_{tool}^{path} - (d_{tool}^{path} \cdot n_{scan}^{path}) n_{scan}^{path},$$

where $d_{tool}^{path}$ is a translational direction of the tip of the surgical tool in $C_{robot}$ and $n_{scan}^{path}$ is a translational direction of the surgical path in $C_{scan}$. The rotational error quantity of the robot movement quantity is determined by the following formula:

$$e_{rot} = \frac{r_{tool}^{path}}{\|r_{tool}^{path}\|} \cos^{-1}\left(\frac{n_{scan}^{path} \cdot n_{scan}^{tool}}{\|n_{scan}^{path}\| \|n_{scan}^{tool}\|}\right)$$

where $r_{tool}^{path}$ is a rotational component of the surgical path in in $C_{robot}$, $n_{scan}^{tool}$ is a translational direction of the tip of the surgical tool in $C_{scan}$, and $n_{scan}^{path}$ is a translational direction of the surgical path in $C_{scan}$.

Once the robot movement quantity is calculated and the alignment error between the surgical tool and the surgical path is below a preset threshold, the surgical tool is moved with the robot arm in a position and direction corresponding to the surgical path using the robot movement quantity, thereby performing the drilling operation. The surgical path is preferably continuously tracked by the surface scanner while aligning the surgical tool to the surgical path and moving the surgical tool with the robot arm in the position and direction corresponding to the surgical path.

The reference numbers in the figures have the following meanings:

| Component | Subcomponent | Reference Number |
|---|---|---|
| robot arm | | 100 |
| | distal end | 101 |
| surgical tool | | 110 |
| | proximal end | 108 |
| | distal end | 109 |
| electric drill | | 111 |
| drill guide | | 114 |
| drill head | | 119 |
| | sleeve | 112 |
| | horn-like distal end | 113 |
| | cone-shaped distal end | 115 |
| | circumferential grooves | 116 |
| | circumferential ridges | 117 |
| drill bit | | 118 |
| surface scanning equipment | | 200 |
| field of view | | 210 |
| workstation | | 300 |
| graphical user interface | | 310 |
| surgical target | | 400 |
| data cables | | 500 |

DETAILED DESCRIPTION

Hereinafter, the exemplary embodiments of the invention are described in detail in combination with the accompanying drawings. For clarity and concision, the specification does not describe all the features of practical implementations. However, it should be understood that, in the process of developing any practical embodiments, many implementation-specific decisions must be made to achieve the specific targets of developers, for instance, to be in line with those limiting conditions that are related to a system and business, and these limiting conditions may change with the different implementations. It also has to be understood that although such development work may be complex and take long time, the development work is merely a routine task for those of skill in the art having the benefit of this disclosure.

Here, it should be noted that for preventing unnecessary details from obscuring the invention, only device structures, methods and processing steps that are closely related to the scheme according to the invention are illustrated in the accompanying drawings and description, and the representations and the descriptions of parts, algorithms, software, and processing that are little related to the invention and known by those of ordinary skill in the art are omitted.

Definitions

As used herein, the following terms and variations thereof have the meanings given below, unless a different meaning is clearly intended by the context in which such term is used.

"2D" refers to two-dimensional areas, images, or other representations of two-dimensional areas. Images on a computer monitor are two-dimensional. "3D" refers to three-dimensional spaces or to representations of three-dimensional spaces.

"Computer" refers to a device for storing and processing data.

"Drill bit" refers to the cutting portion of a drill.

"Drill head" refers to the part of a drill which secures a drill bit to the drill.

"Drill guide" refers to a hollow cylinder that restricts the position and direction of a drill bit.

"Flaring" refers to a shape which has a diameter that increases as the shape extends longitudinally outwardly, i.e. away from a narrower diameter portion.

"Kinematic data" refers to data concerning the dimensions, geometries and/or positioning of the links of a robot arm, the positioning of a tool coordinate frame with respect to the tool flange of the robot arm, and to the angles of each joint of a robot arm. The position of the tool coordinate frame with respect to the tool flange of a robot arm is generally obtained from tool calibration, a routine procedure for industrial robot arms, and the joint angles of a robot arm are obtained from encoders at each joint. The position of the tool coordinate frame with respect to a robot base can be calculated with kinematic data. Robot kinematics, is known to those of skill of the art (for example in Corke, P (2017) Robotics, vision and control: fundamental algorithms in MATLAB®, vol 118, 2nd edn. Springer, Berlin).

"Matte surface" refers to a surface which reflects light diffusely.

"Observing" or "viewing", with respect to a scanner, refers to the receipt of signals (such as electromagnetic signals) by a scanner from a defined surface or area.

"Path," in reference to a surgical tool, refers to the spatial coordinates along which the surgical tool is moved during a surgical procedure, such as by a robot arm.

"Register" and "registration" refer to image registration, i.e. to a process of transforming different sets of image and/or spatial data into one coordinate system, for example to map (align) the points in one image to points in another image.

"Workstation" refers to a computer having a graphical user interface (GUI).

The terms "above," "below," "between," and other terms of relative position or orientation as used herein refer to a relative position of one component of the present system (or a subject being treated with the system) with respect to others.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise. Ranges which are described as being "between" two values include the indicated values.

System

The present invention provides a surface tracking-based surgical robot system for drilling operations together with a feedback control method which overcomes deficiencies in prior technologies, such as complicated and time-consuming workflows and imperceptible positioning errors.

The present system preferably comprises a robot arm with a surgical tool as its end-effector, surface scanning equipment, and a computer in communication with a graphical user interface (i.e., a workstation) for doctors to interact with the system and control software running on it. The robot arm has at least three translational degrees of freedom and at least two rotational degrees of freedom. For example, a six degree of freedom robot arm can be used. The workstation of the system comprises the system components that provide processing and control functions and is in communication with the surface scanning equipment, robot arm and other system components, such as with data cables or through wireless connections. The workstation is used to process scanned data, plan a drilling path, visualize the tracking error and control the motion of the robot arm. The surface scanning equipment can provide surface geometry and color information of the surgical site and the surgical tool, and can include a Time-of-Flight (ToF) camera, a structured light camera, a laser scanner, and/or other components. The surgical tool is preferably designed for robust and accurate tracking.

Figure 1:
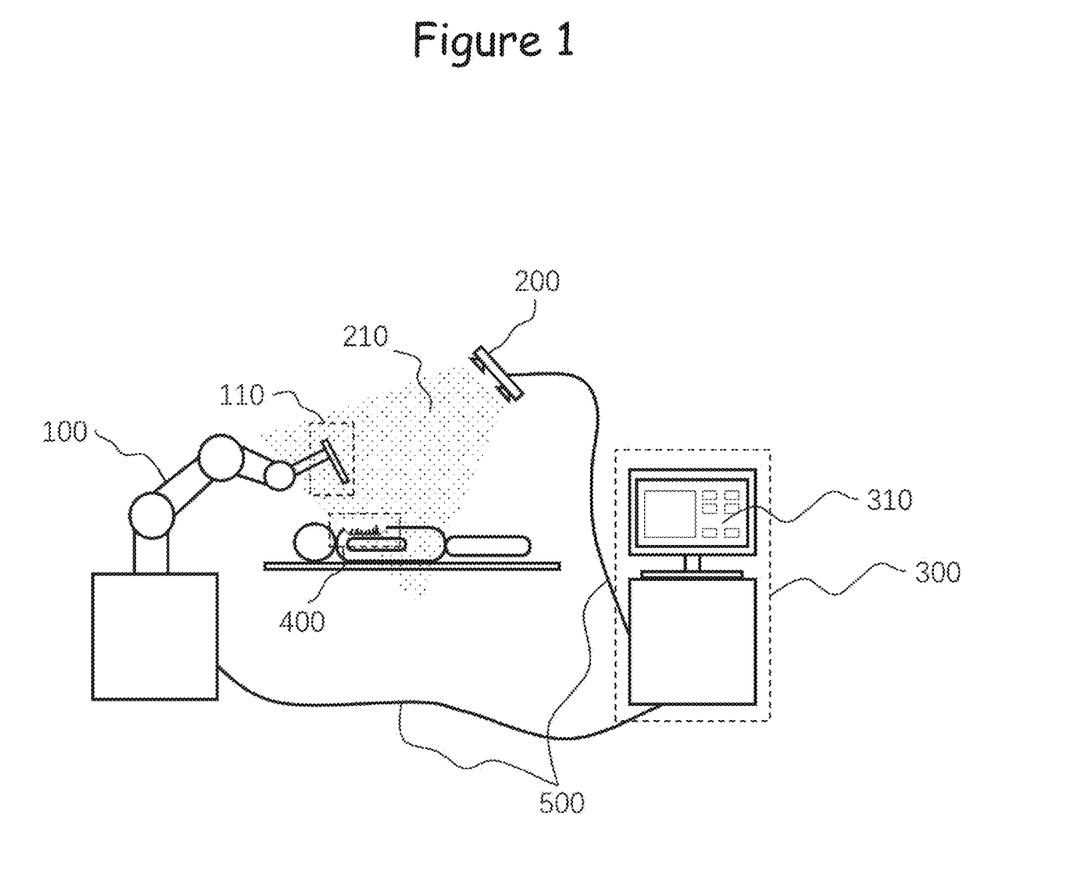
FIG. 1 is a schematic drawing of the components in an embodiment of the present system.

FIG. 1 illustrates components of the present surface tracking-based surgical robot system for drilling operations. The system comprises a robot arm 100, a surgical tool 110 attached to the end of the robot arm, a surface scanner (scanning equipment) 200 and a workstation 300. The robot arm has at least three translational degrees of freedom and two rotational degrees of freedom. The surface scanning equipment is preferably capable of acquiring surface geometry and color information of the surgery site and a surgical tool simultaneously, and can include (but is not restricted to) a laser scanner, a ToF (time-of-flight) camera, and/or a structured light camera/scanner, and is used to track the position and orientation of the surgical tool 110 and also the surgical target 400 (a subject undergoing surgery) simultaneously. The surgical tool 110 has a proximal end 108 and a distal end 109, and is attached at its proximal end 108 to the distal end 101 of the robot arm 100. The surgical tool 110 is preferably specially designed for robust and accurate tracking by the surface scanning equipment 200. The workstation 300 is in communication with the surface scanning equipment 200 and the robot arm 100, such as through a wired connection with data cables 500 or through a wireless network and is used to plan the drilling path, visualize the tracking error through the graphical user interface 310, process the scanned data, and control the motion of the robot arm.

Figure 2:
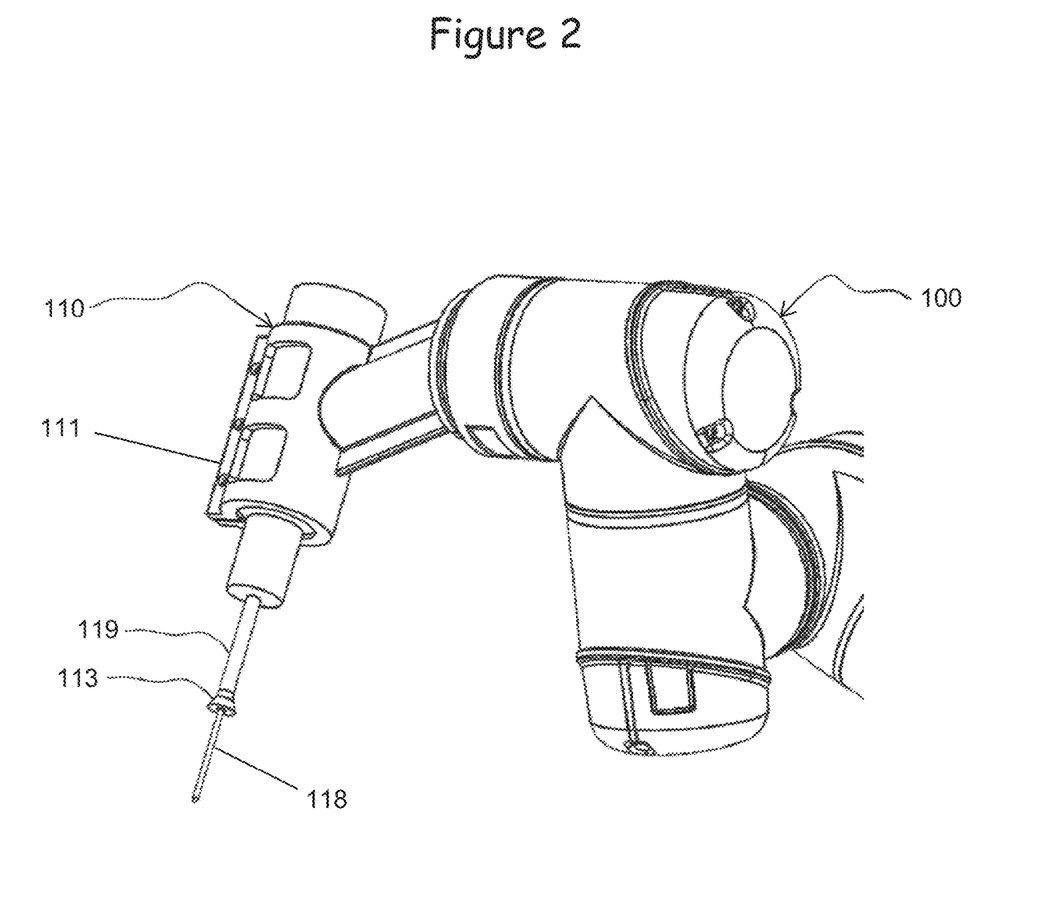
FIG. 2 is a perspective view of an electric drill attached to the end of a robot arm.
Figure 3:
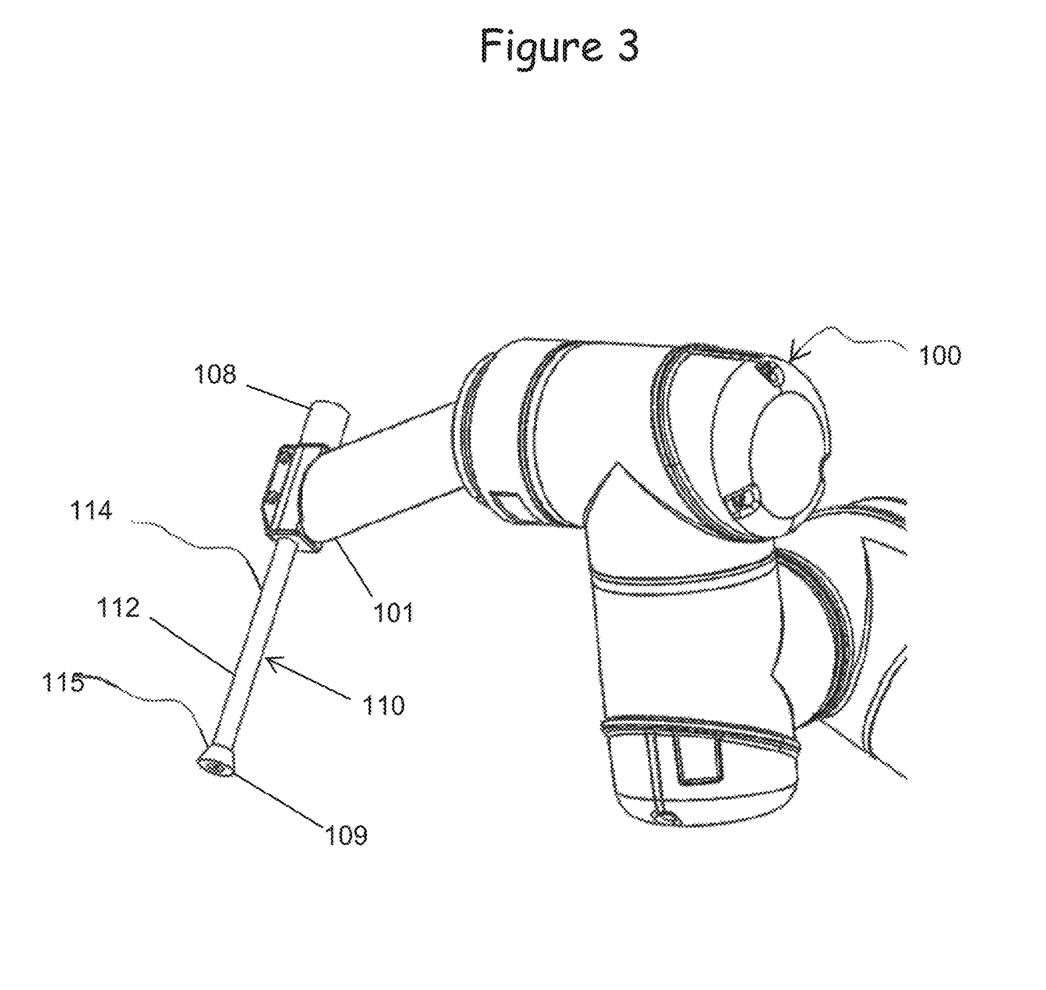
FIG. 3 is a perspective view of a drill guide attached to the end of a robot arm.
Figure 4:
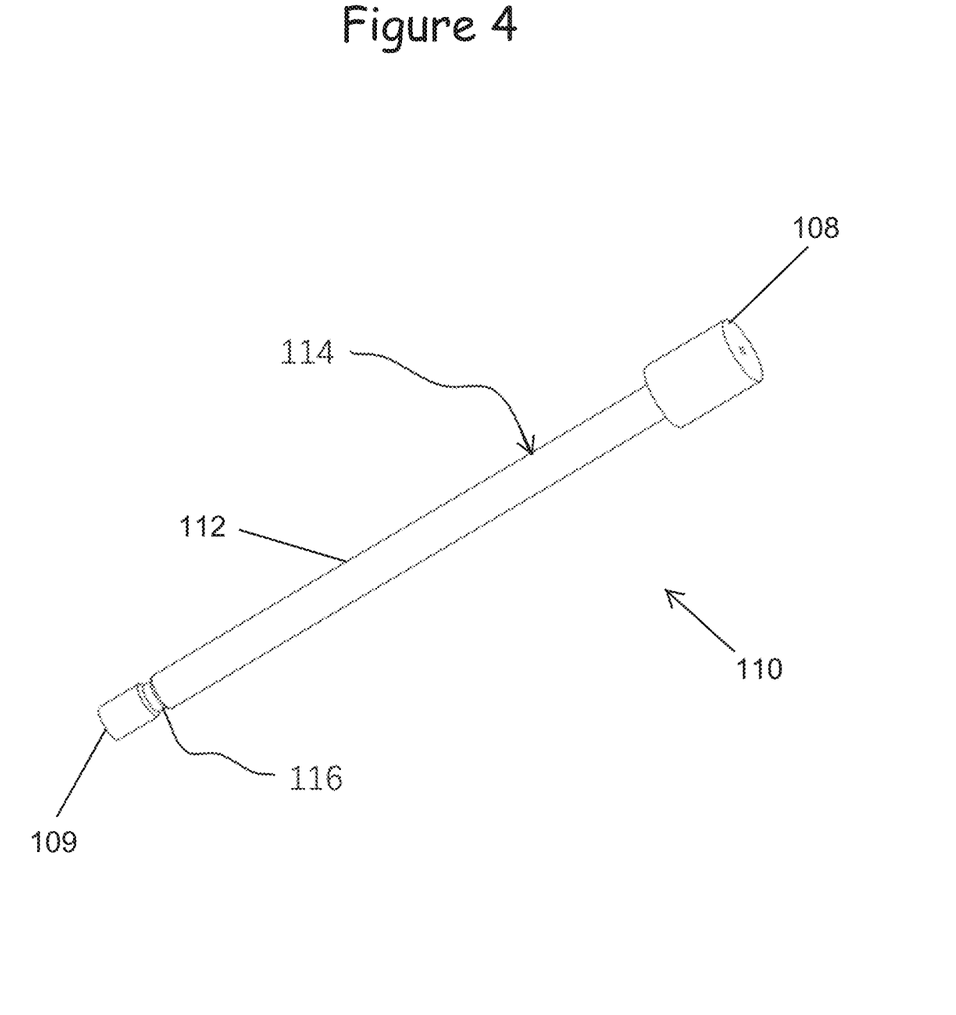
FIG. 4 is a perspective view of one embodiment of a drill guide.
Figure 5:
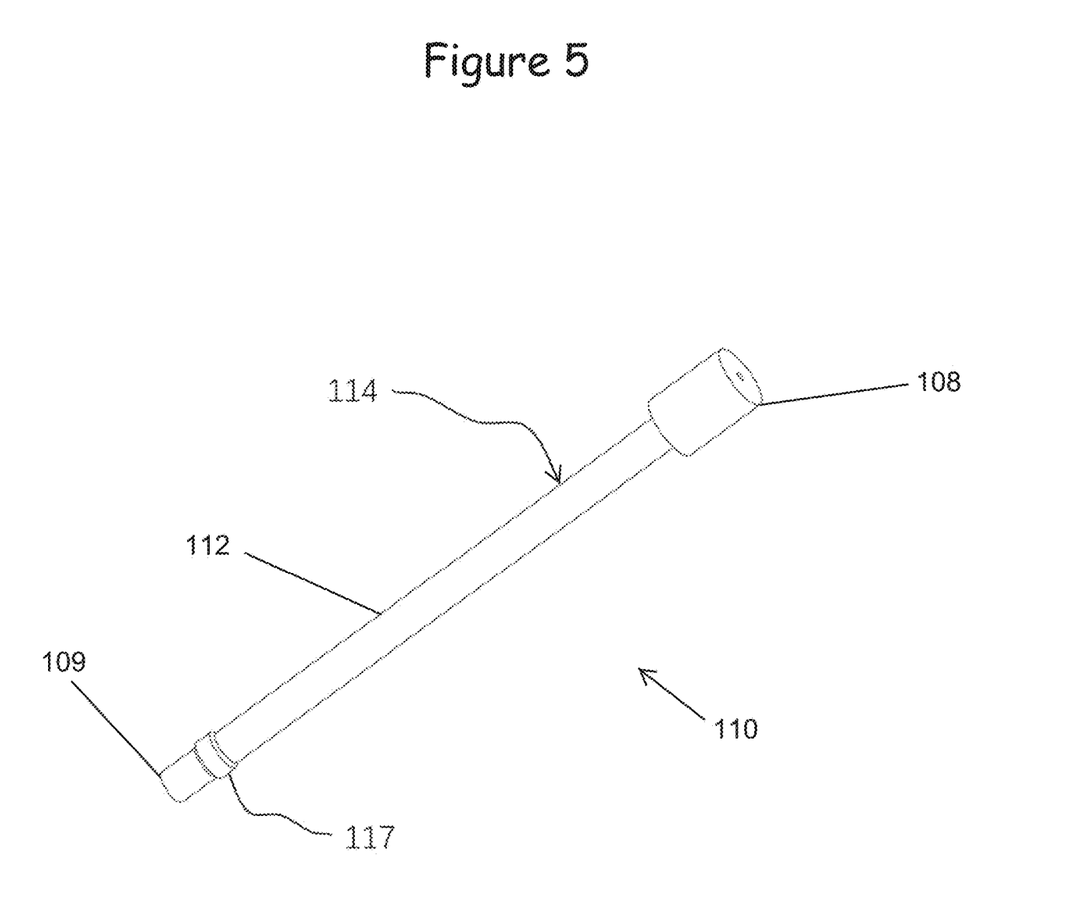
FIG. 5 is a perspective view of another embodiment of a drill guide.

FIGS. 2-5 are illustrations of examples of surgical tools 110 for use in the system shown in FIG. 1. In FIG. 2, the surgical tool 110 attached to the robot arm 100 is an electric drill 111. In FIG. 3, the surgical tool attached to the robot arm 100 is a drill guide 114. Ordinary drill guides and drill heads are cylindrical, but the drill guide 114 and drill head 119 in the provided system are preferably designed for robust and accurate tracking by the surface scanning equipment. FIGS. 2-5 show examples of modified drill guides 114 and drill heads 119. In the example shown in FIG. 3, a sleeve 112, preferably a 3D-printed sleeve, is attached to the robot arm 110. In this example, the outer surface of the 3D-printed sleeve 112 can be painted or otherwise provided with a matte color (such as green) for better surface scanning quality. To make the sleeve 112 more distinctive along the axial direction, the sleeve 112 is provided with a distal end 113 which has a distally (outwardly) flaring or horn-like shape. A similar flaring component can be provided on the distal end of a cylindrical portion of a drill head 119. The distally flaring-shaped component can comprise any number of configurations which extend laterally outwardly toward the distal end of the surgical tool 110, such as a conical shape, a frustoconical shape, a hemispherical shape, or bell shape. FIG. 3 illustrates a frustoconical distal end 115 of the surgical tool 110. surgical tools 110 can alternatively include single or multiple circumferential grooves 116, such as on the sleeve 112 shown in FIG. 4, or single or multiple circumferential ridges 117 as shown in FIG. 5. Combinations of shaped components located at the distal end 109 of a surgical tool 110, such as those shown in FIGS. 2-5, can also be used.

Process

In the present process, the surgery workflow using a system such as the system described above is preferably as follows. 3D image data of a target surgery area is preoperatively acquired with an imaging device, such as a CT or MRI machine, and a surgical path is planned on the acquired 3D image. Surface geometry of the target surgery area is then extracted from the acquired 3D image data and preprocessed for surface tracking, preferably including down-sampling of the data and removal of the part that is invisible from the surface scanning equipment.

During the intraoperative stage, the surface scanning equipment is placed into a proper position so that the surgery target is in the field of view of the surface scanning equipment and so that the surgical tool held by the robot arm is also in the field of view of the surface scanning equipment. The surface scanning equipment constantly acquires the surface geometry and color information of the surgical site and the surgical tool during an operation.

The target surface area on a subject is then manually selected by the surgeon(s) on a color image extracted from the scan data through the graphical user interface of a connected workstation, and the corresponding area in the scanned geometry data is automatically segmented out according to the 2D-3D correspondence of the scan data. The robot arm is then registered to the surface scanning equipment using an SVD (Singular Value Decomposition)-based method.

The robot arm aligns the held surgical tool to the preoperatively planned surgical path using a feedback control method according to the relative position between the surgical path and the surgical tool tracked by the surface scanning equipment. In an automatic drilling mode, the surgical tool held by the robot arm is an electric drill, which spins and moves along the surgical path driven by the robot arm. The depth and speed of the drilling operation is assigned by the surgeon through the graphical user interface on the workstation. In a manual drilling mode, the surgical tool held by the robot arm is a drill guide, through which the surgeon manually drills the hole.

Figure 6:
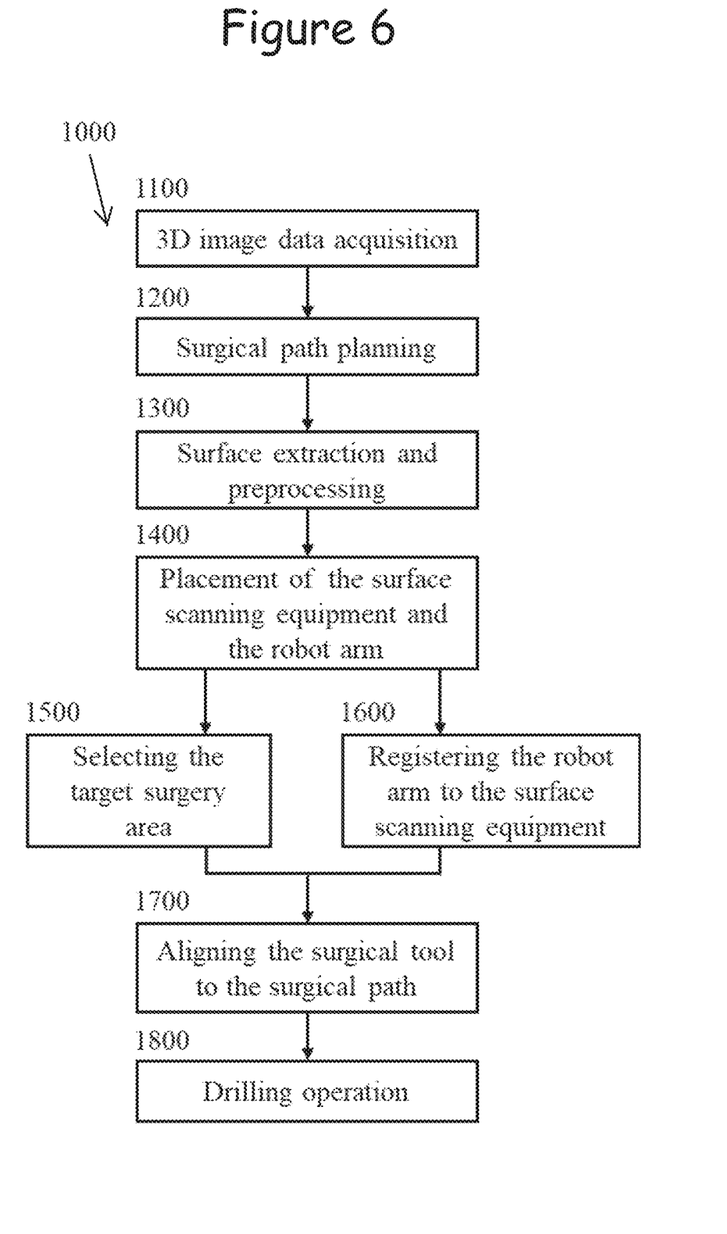
FIG. 6 is a flowchart of one embodiment of a feedback control method for use with the present system.

FIG. 6 is a block diagram of one embodiment of a robot-assisted surgical method 1000 for a drilling operation using a surface tracking-based surgical robot system as described herein.

In step 1100, 3D image data of the target surgery area is acquired. A 3D image acquisition device includes but not restricted to CT and MRI machine;

In step 1200, the surgical path is planned on the 3D image data acquired in 1100, which is represented with the position of the entry point and the direction of the surgical path in the image coordinate frame, $C_{image}$;

In step 1300, the surface geometry of the target surgery area is extracted from the 3D image data acquired in 1100 including but not restricted to point clouds, triangular facets and meshes. Then the surface geometry data is preprocessed, including down-sampling of the data and removal of the part that is invisible from the surface scanning equipment.

In step 1400, the surface scanning equipment 200 is placed into a proper position so that the target surgery area 400 is in the field of view 210 (FIG. 1) of the surface scanning equipment 200. Then the robot arm 100 is also moved to a proper position so that the surgical tool 110 is in the field of view 210 of the surface scanning equipment 200.

In step 1500, the target surgery area is selected on the 2D color image extracted from the latest scanning data. As mentioned above, the surface scanning equipment can provide not only surface geometry but also color information of the surgery area, and the color information and the geometry information can be aligned together. The surgeon selects the target surgery area by drawing a contour on the color image shown on the graphical user interface 310, then the surface of the target surgery area is segmented from the raw scanned surface data according to this selected area and the correspondence between the color data and the surface geometry data. In a more specific example, the scanned geometry information is represented with a point cloud and the color image information is represented with a 2D color image. The points in the point cloud have a one-to-one correspondence to the pixels in the 2D color image. After a target surgery area is selected from the 2D color image, the surface of the target area is segmented from the point cloud according to the aforementioned one-to-one correspondence. Segmentation involves separating data corresponding to the area of interest, e.g. the area being operated on, from other data being gathered during the process, such as raw data from a 2D image or a 3D point cloud. Methods of segmenting data are known to those of skill in the art (see, e.g., Gonzalez, R C, et al., Digital Image Processing (3rd Edition), Prentice-Hall, Inc. 2007). Segmentation can be performed manually or automatically.

A number of algorithms known to those of skill in the art in the field of robotics can be used to align the segmented scanned surface data of step 1500 to the preprocessed surface data of step 1300. For example, the "4PCS" (4-points congruent sets) method (Aiger D, Mitra N J (2008) "Cohen-Or D 4-points congruent sets for robust pairwise surface registration," ACM SIGGRAPH 2008 papers, Los Angeles, Calif. ACM, 1360684, pp 1-10) or the "Super4PCS" method (Mellado N, et al. (2014) "Super 4PCS fast global point cloud registration via smart indexing," Comput Graph Forum 33(5):205-215) can be used to find an initial alignment of the preprocessed point clouds automatically. The 4PCS method finds all possible candidates of rigid transformation defined by "coplanar 4-point sets" and then chooses the best candidate. The Super4PCS method speeds up the 4PCS method via a smart indexing technique. Other methods, such as those described in U.S. patent Ser. No. 10/217,277 to Luc Franck Robert, et al., can also be used.

In step 1600, the robot arm 100 is registered to the surface scanning equipment, i.e., the rotation matrix (denoted as $R_{robot}^{scan}$) from the base coordinate frame of the robot arm (denoted as $C_{robot}$) to the coordinate frame of the surface scanning equipment (denoted as $C_{scan}$) is calculated. Steps 1500 and 1600 are parallel, and can be performed either serially or parallelly.

Figure 7:
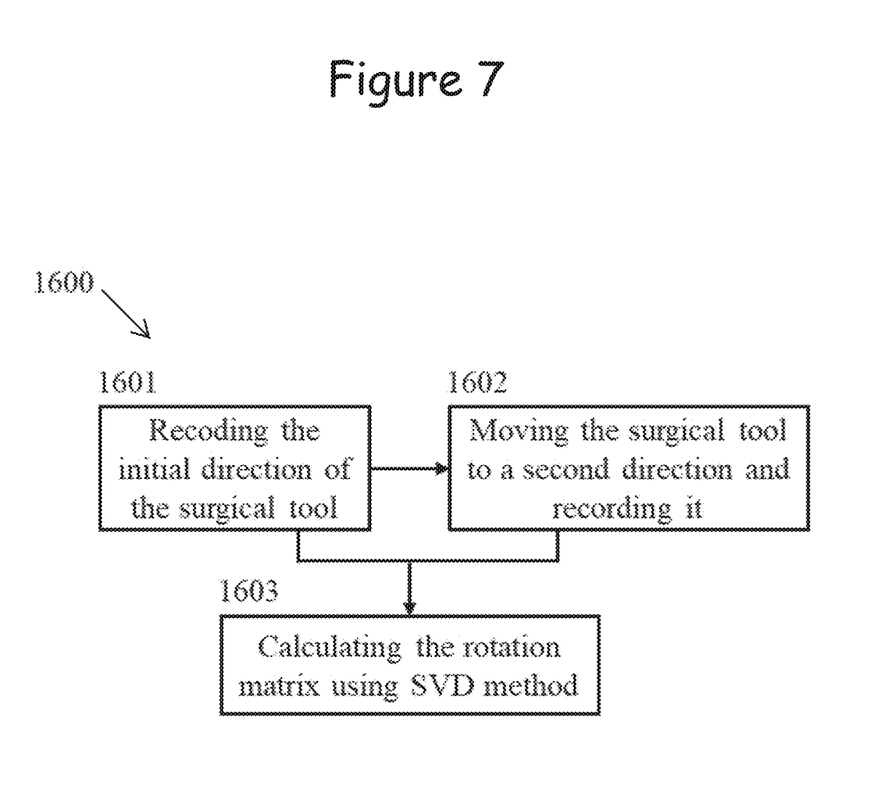
FIG. 7 is a flowchart of one embodiment of a registration process for use with the present system.

In step 1600 of the above embodiment, the rotation matrix $R_{robot}^{scan}$ is calculated as shown in FIG. 7:

In substep 1601, the initial direction of the surgical in both $C_{robot}$ and $C_{scan}$ is acquired and recorded.

In substep 1602, the surgical tool is pointed to a second direction, and the direction of the surgical tool in both $C_{robot}$ and $C_{scan}$ is acquired and recorded.

In substep 1601 and 1602, the directions of the surgical tool in $C_{scan}$ are tracked by the surface scanning equipment as described in the above embodiment and are denoted as $(n_{scan}^{tool})_1$ and $(n_{scan}^{tool})_2$ respectively. The directions of the surgical tool in $C_{robot}$ are obtained with robot kinematics and are denoted as $(n_{robot}^{tool})_1$ and $(n_{robot}^{tool})_2$ respectively.

In substep 1603, the rotation matrix $R_{robot}^{scan}$ is obtained by solving the flowing extreme-value problem using the SVD (Singular Value Decomposition) method:

$$R_{robot}^{scan} = \underset{R \in \text{Rotation matrix}}{\arg\min} \sum_{i=1,2} \|R(n_{robot}^{tool})_i - (n_{scan}^{tool})_i\|$$

In step 1700, according to the relative spatial relationship between the surgical path and the surgical tool, the robot movement quantity is calculated using a feedback control method, and the robot arm moves accordingly. This step is repeated until the error of the alignment from the surgical path to the surgical tool is below a preset threshold.

In step 1700, the position and direction of the surgical path is tracked by the surface scanning equipment. $p_{image}^{path}$ and $n_{image}^{path}$ denote the entry point position and direction of the surgical path in the image coordinate frame $C_{image}$ defined in step 1100 respectively, $p_{scan}^{path}$ and $n_{scan}^{path}$ denote the entry point position and direction of the surgical path in the coordinate frame of the surface scanning equipment $C_{scan}$ respectively. The transformation from $C_{image}$ to $C_{scan}$ (represented with the rotation matrix $R_{image}^{scan}$ and the translation vector $d_{image}^{scan}$) is obtained by aligning the segmented scanned surface data of step 1500 to the preprocessed surface data of step 1300 using surface registration algorithms.

After this, the position and direction of the surgical path in $C_{scan}$ is obtained using the following formulas:

$$p_{scan}^{path} = R_{image}^{scan} p_{image}^{path} + d_{image}^{scan}$$

$$n_{scan}^{path} = R_{image}^{scan} n_{image}^{path}$$

In step 1700 of the above embodiment, the relative spatial relationship between the surgical tool and the surgical path is defined by the translational part $d_{tool}^{path}$ and the rotational part $r_{tool}^{path}$, wherein $$d_{tool}^{path} = p_{scan}^{path} - p_{scan}^{tool}$$

$$r_{tool}^{path} = n_{scan}^{path} \times n_{scan}^{tool}$$

The alignment error is defined by the translational error $e_{trans}$ and the rotational error $e_{rot}$, wherein $$e_{trans} = d_{tool}^{path} - (d_{tool}^{path} \cdot n_{scan}^{path}) n_{scan}^{path}$$

$$e_{rot} = \frac{r_{tool}^{path}}{\|r_{tool}^{path}\|} \cos^{-1}\left(\frac{n_{scan}^{path} \cdot n_{scan}^{tool}}{\|n_{scan}^{path}\| \|n_{scan}^{tool}\|}\right)$$

Then the robot movement quantity is given by $$d_{robot} = (R_{robot}^{scan})^T e_{trans}$$

$$r_{robot} = (R_{robot}^{scan})^T e_{rot}$$

wherein $R_{robot}^{scan}$ is acquired in step 1600, $d_{robot}$ denotes the translation of the robot in $C_{robot}$, the direction of $r_{robot}$ indicates the rotation axis in $C_{robot}$ of the robot arm with respect to the tip of the surgical tool, "T" indicates a transposition of the matrix/vector, and the amplitude of $r_{robot}$ represents the rotation angle of the robot arm along the rotation axis.

In step 1800 of the above embodiment, position and orientation of the surgical tool is tracked by the surface scanning equipment. $p_{model}^{tool}$ and $n_{model}^{tool}$ denote the tip position and direction of the surgical tool in the coordinate frame of the CAD model of the surgical tool $C_{model}$, respectively, $p_{scan}^{tool}$ and $n_{scan}^{tool}$ denote the tip position and direction of the surgical tool in the coordinate frame of the surface scanning equipment $C_{scan}$ respectively. The transformation from $C_{model}$ to $C_{scan}$ (represented with the rotation matrix $R_{model}^{scan}$ and the translation vector $d_{model}^{scan}$) is obtained by aligning the segmented scanned surface data of the surgical tool to the surface of the CAD model of the surgical tool using the surface registration algorithms. Then the position and direction of the surgical tool in $C_{scan}$ is obtained by $$p_{scan}^{tool} = R_{model}^{scan} p_{model}^{tool} + d_{model}^{scan}$$

$$n_{scan}^{tool} = R_{model}^{scan} n_{model}^{tool}$$

In the above embodiment, data can be segmented in order to speed up the surface registration process and make it more robust, thereby improving the accuracy of the process. An example of segmentation of the surface data of the surgical tool from the scanned data comprises the following steps:

Firstly, the color image extracted from the latest scanned data is converted to HSV(Hue-Saturation-Value) color space. The pixels of the surgical tool are coarsely segmented out by binarizing the H channel of the HSV image according to the color of the surgical tool. Then the result is refined through morphologic operation on the binarized H channel, including filling the vacancies and removing the small areas.

Secondly, the selected pixels of the surgical tool are mapped to the scanned surface data and the corresponding surface data is segmented out.

In step 1800, a hole is drilled along the planned surgical path. Two modes are provided in this system. For automatic drilling mode, the robot arm moves the electric drill 111 along the axil direction of the drill bit to execute the drilling operation. The depth and speed of the drilling operation is assigned by the surgeon through the graphical user interface 310 on the workstation 300. For manual drilling mode, the surgeon manually drills the hole through the drill guide 114 held by the robot arm.

The present system can be used for a variety of surgical operations which involve drilling, but it is particularly useful for operations on the spine. The features and benefits of the present invention include the following:

User-friendliness. The hardware configuration and workflow of the present system doesn't rely on any optical positioning equipment. Therefore, the process of optical marker installation and registration is avoided. For aspect of surface tracking, the present system has a higher level of automation compared with other surgical systems using the surface registration technology, due to an improved surface registration strategy and the use of specially designed surgical tools.

Safety. The tracking error in the present system can be visualized on a graphical user interface, as the surgery target and the surgical tool are directly tracked through their surface information. In this way, the safety of the system is improved compared with optical positioning-based systems in which the systematic error is difficult to detect.

Improved accuracy. As the surgery target and the surgical tool are tracked with the same surface scanning equipment, the relative spatial relationship between the surgery target and the surgical tool is directly acquired. Along with the feedback control method based on this relative spatial relationship, the ultimate accuracy of the system is limited only by the tracking accuracy, regardless of the errors from robot registration, robot kinematics and surgical tool calibration, and such errors can be compensated for. By contrast, in an optical positioning-based system, these errors will accumulate along the coordinate transformation chain.

EXAMPLES

Example 1. Registration of a Prototype System

A prototype system was built to validate the feasibility of the present method. The prototype system which included a 6-DOF industrial robot arm (UR5e, Universal Robots A/S, Denmark), a consumer-grade structured light camera (AiLook, Chishine Technology Co., Ltd, China), and a mobile workstation (ThinkPad P53, Lenovo group Co., Ltd, China). The camera provided 640×400 RGB-D images (aligned RGB and Depth images) with 0.1 mm depth resolution at 10 frames per second. The registration algorithms and control software were implemented with C++ and Matlab. The CT machine (uCT760, Shanghai United Imaging Healthcare Co., Ltd, China) used for preoperative data acquisition and postoperative evaluation had a pixel size of 0.32 mm and a slice thickness of 1 mm.

Polymeric phantoms (models) of cervical vertebrae (C1 to C7) were tested in this study. The phantoms were applied with plasticine to simulate the soft tissues covering the bone surface. Only laminae, the superior surface of lateral mass, and spinous processes were exposed. To test the robustness of the tracking algorithm, the phantoms were scanned from five different view angles. The SRE (Surface Registration Error, distance from a point in the scanned point cloud to the closest point in the registered model point cloud) was superimposed onto the color image. The RMS (Root Mean Square) of SRE was 0.1030 mm.

The position and orientation of bone anatomy with respect to the camera were tracked by registering the model point cloud to a scanned point cloud. We used the ICP (Iterative Closest Point) method, a commonly used algorithm for point cloud registration through which the point clouds are aligned by iteratively optimizing the rigid transformation and updating the point pair correspondence. However, a coarse alignment was used to guarantee the correct convergence of the ICP-based methods. A feasible approach for coarse alignment was manually matching some anatomic landmarks, which, however, would increase the surgery time. Besides the initial coarse alignment, a low overlap ratio was another challenge, as only a limited area of the bone surface is exposed in spine surgery. This is more difficult than the facial registration in a neuro/maxillofacial surgery, in which the whole face is visible to the camera.

In this study, we solved point cloud registration problems by firstly preprocessing the point clouds to increase their overlap ratio and then accomplishing the registration through a coarse-to-fine strategy.

For the model point cloud, after being extracted from the raw CT data, the lower half of the vertebrae was simply removed, as only the upper half is visible to the camera. For the scanned point cloud, the target vertebra was coarsely annotated by the surgeon on the 2D image and then mapped to the 3D point cloud. A Super4PCS algorithm was then used to find an initial alignment of the preprocessed point clouds automatically. The 4PCS (4-points congruent sets) method works by finding all the possible candidates of rigid transformation defined by "coplanar 4-point sets" and then choosing the best candidate. The Super4PCS method speeds up the 4PCS method via a smart indexing technique, which performs well in both speed and robustness compared with other algorithms for coarse point cloud registration, as reviewed by Díez et al. Given the coarse initial alignment, the preprocessed point clouds are then accurately aligned using the classic ICP method.

Point clouds of the surgical tool used in this study, a drill guide, were also preprocessed before registration to increase their overlap ratio. For the model point cloud, half of the tool was removed as only one side of it was visible from the camera. For the scanned point cloud, the tool was segmented from the raw point cloud through its distinctive color. This segmentation was performed on the color image through HSV (Hue-Saturation-Value) analysis and morphologic operations, and the segmented area is then mapped to the point cloud. The preprocessed point clouds were then registered through the same coarse-to-fine process as that used for bone anatomy tracking.

Example 4. Surgical Tool Tracking

The trackable angle of the surgical tool can best be tracked by the camera when the angle between the tool direction and the line of sight ranges from about 20° to 120°. The RMS of SRE in this test was 0.075 mm. The tool tracking accuracy was tested using the robot arm as a reference. The robot arm moved the tool tip to traverse a spatial cubic array (75×75×75 mm, 25 mm step size, 64 points in total) in the robot base coordinate frame $C_{robot}$. The traversed positions were tracked by the camera, which formed another cubic array in the camera coordinate frame $C_{cam}$. The robot arm traversed the cubic array with pure translation, which excluded the influence of tool calibration error. The tracked cubic array in $C_{cam}$ was aligned to the reference cubic array in $C_{robot}$ using the SVD method. The alignment RMSE is 0.17 mm, and the SD of tracked tool directions in $C_{cam}$ was 0.17°.

The tracking error was also analyzed. Since the phantoms were static during the tracking experiment, relative positions between each registered vertebra point cloud should not change with different view angles. In other words, tracking results of different view angles should be consistent with each other. To test their consistency, the registered model point clouds of each scan were aligned together with the least square method, and the results are listed in Table 2 below, in which the largest standard deviation (SD) is 0.10 mm for vertebra center position, and 0.49° for vertebra orientation:

TABLE 2

Position and attitude consistency between registered model point clouds

| | Vertebra number | | | | | | | |
|---|---|---|---|---|---|---|---|---|
| | C1 | C2 | C3 | C4 | C5 | C6 | C7 | Overall |
| Position SD (mm) | 0.10 | 0.08 | 0.07 | 0.07 | 0.04 | 0.08 | 0.10 | 0.08 |
| Orientation SD (°) | 0.50 | 0.22 | 0.34 | 0.25 | 0.28 | 0.29 | 0.30 | 0.32 |

The results demonstrate satisfactory tracking accuracy of the present tracking method and its robustness to partially exposed surface and different view angles.

Example 3. Robot Control

Figure 8:
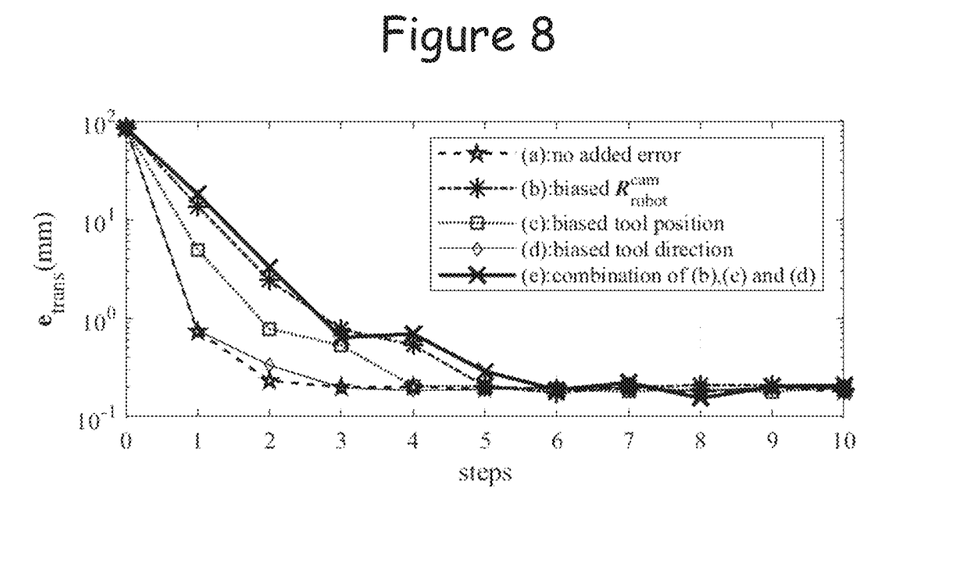
FIG. 8 is a table showing the results of a first robot control test performed by aligning a surgical tool to a virtual target surgical path.
Figure 9:
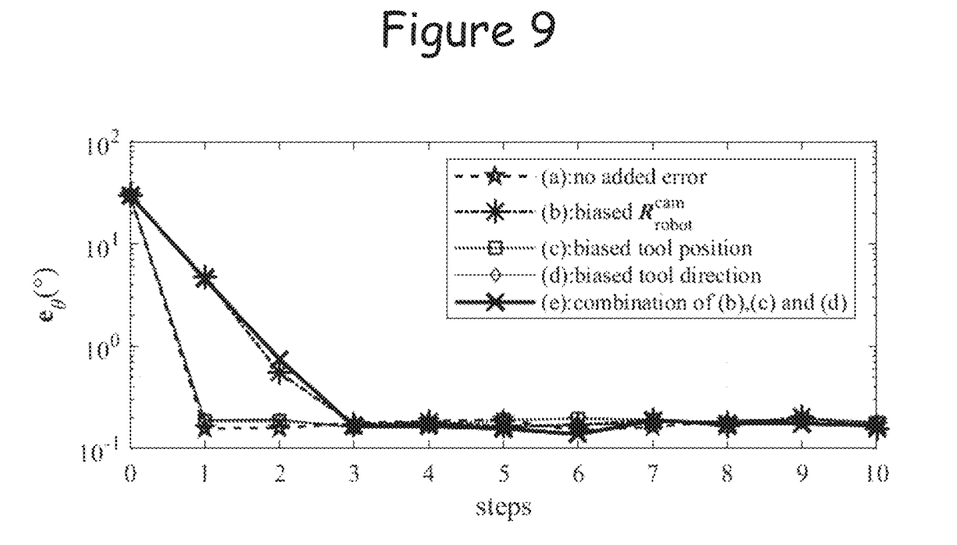
FIG. 9 is a table showing the results of a second robot control test performed by aligning a surgical tool to a virtual target surgical path.

A robot control test was performed by aligning the surgical tool to a virtual target surgical path defined in $C_{cam}$. Possible error sources were considered including the error of $R_{robot}^{cam}$ and surgical tool calibration (tool tip position and tool direction with respect to the robot's tool flange). Starting from the same initial position, five conditions were tested: (a) no artificially added error; (b) $R_{robot}^{cam}$ rotated by 10° along arbitrary directions; (c) tool tip offset by 10 mm along arbitrary directions; (d) tool direction deflected by 10° along arbitrary directions; (e) combination of (b), (c) and (d). As shown in FIGS. 8 and 9, even in the presence of both robot-camera registration and tool calibration error, after just a few steps the alignment error was reduced to a low level that is trackable by the camera. The results indicate that the final alignment accuracy is only limited by the structured light tracking accuracy, regardless of the error of robot-camera registration and tool calibration.

Example 4. Drilling Experiments

Drilling experiments for pedicle screw placement were performed on three cervical vertebrae phantoms. A total of 42 paths were planned by two surgeons and then manually drilled through the drill guide using a 2 mm-diameter drill. Besides the plasticine, we also applied some tomato sauce to the 3rd phantom (FIG. 14) to test the influence of residual soft tissues and reflective liquid on the bone surface.

Figure 10:
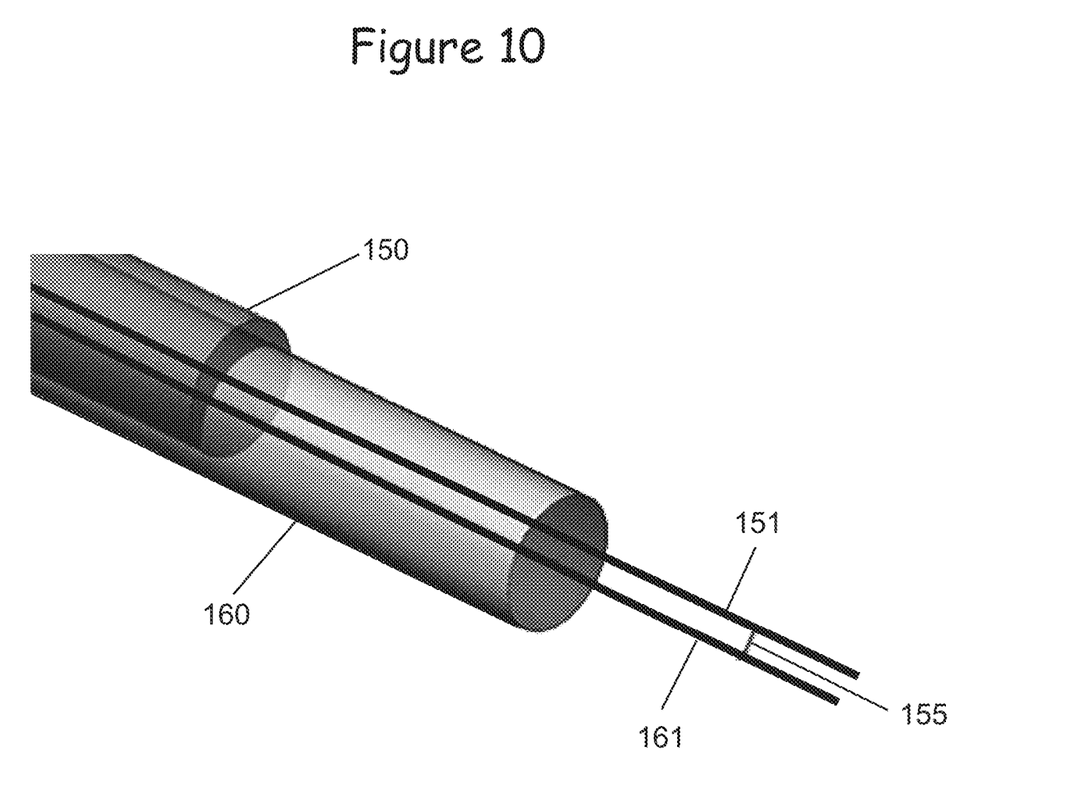
FIG. 10 is an illustration of drilling angle error.

After the drilling experiments, a postoperative CT scan was performed. The drilling error (position error and angle error) was calculated by registering the preoperative CT data to the postoperative one and comparing the actual drilled paths with the planned paths. Position error is defined as the distance between the planned and actual entry points, while angle error is defined as the angle between the planned and actual drilling paths. Angle error is illustrated in FIG. 10, where line 151 represents a hypothetical line extending through the center of the planned drill path 150, line 161 represents a hypothetical line extending through the center of the surgical tool 160, and angle 155 between these two lines is the angle error. The results are listed in Table 3 below.

TABLE 3

Results of Drilling Experiments

| | Phantom #1 | | Phantom #2 | | Phantom #3 (applied with tomato sauce) | |
|---|---|---|---|---|---|---|
| Vertebra and side | Position error (mm) | Angle error (°) | Position error (mm) | Angle error (°) | Position error (mm) | Angle error (°) |
| C1-L | 0.43 | 0.80 | 0.19 | 0.94 | 0.15 | 0.53 |
| C1-R | 0.50 | 0.78 | 0.17 | 0.28 | 0.11 | 0.45 |
| C2-L | 0.27 | 0.31 | 0.48 | 0.68 | 0.05 | 0.52 |
| C2-R | 0.64 | 0.27 | 0.30 | 0.41 | 0.29 | 0.50 |
| C3-L | 0.69 | 1.09 | 0.23 | 0.25 | 0.29 | 0.42 |
| C3-R | 0.40 | 0.48 | 0.46 | 0.37 | 0.13 | 0.22 |
| C4-L | 0.22 | 0.66 | 0.06 | 0.62 | 0.16 | 0.10 |
| C4-R | 0.32 | 0.41 | 0.38 | 0.68 | 0.32 | 0.13 |
| C5-L | 0.39 | 0.57 | 0.24 | 0.27 | 0.22 | 0.47 |
| C5-R | 0.15 | 0.97 | 0.30 | 0.18 | 0.37 | 0.54 |
| C6-L | 0.37 | 0.36 | 0.15 | 0.16 | 0.01 | 0.39 |
| C6-R | 0.13 | 0.78 | 0.21 | 0.48 | 0.15 | 0.52 |
| C7-L | 0.53 | 0.53 | 0.42 | 0.70 | 0.14 | 0.58 |
| C7-R | 0.40 | 0.43 | 0.17 | 0.51 | 0.23 | 0.06 |
| Mean | 0.39 | 0.60 | 0.27 | 0.47 | 0.19 | 0.39 |
| SD | 0.17 | 0.25 | 0.13 | 0.23 | 0.10 | 0.18 |

All of the drilled paths were within the pedicles. The mean position error of the entry point was 0.28±0.16 mm, and the mean angle error was 0.49±0.24°, which can satisfy clinical requirements as anatomic studies have shown that the cervical pedicle height ranges from 5.1 to 9.5 mm, and width ranges from 3 to 7.5 mm. Additionally, the applied tomato sauce didn't cause a significant precision reduction, which shows the robustness of the present method to residual soft tissues and reflective liquid on the bone surface.

The examples set forth herein are provided to illustrate certain concepts of the disclosure. The apparatus, devices, or components illustrated above may be configured to perform one or more of the methods, features, or steps described herein. Those of ordinary skill in the art will comprehend that these are merely illustrative in nature, and other examples may fall within the scope of the disclosure and the appended claims. Based on the teachings herein those skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein. The various features and processes described above may be used independently of one another, or may be combined in various ways. All possible combinations and sub-combinations are intended to fall within the scope of this disclosure. In addition, certain steps or features may be omitted in some implementations. All patents, patent publications, and other publications referred to herein are incorporated by reference in their entireties.

What is claimed is:

1. A method for performing a drilling operation on a subject with a surgical robot system, comprising the steps of:
   providing a surface tracking-based surgical robot system comprising a surface scanner, a workstation, and a surgical robot, the surgical robot comprising a robot arm having a surgical tool attached to a distal end of the robot arm, the surgical tool comprising a surgical drill or a drill guide;
   acquiring 3D image data of a target surgery area and planning a surgical path on this 3D image data;
   extracting surface geometry of the target surgery area from the 3D image data to produce surface geometry data;
   positioning the surface scanner so that the target surgery area can be viewed by the surface scanner;
   positioning the robot arm so that the drill guide can be viewed by the surface scanner;
   selecting the target surgery area by creating a contour of the target surgery area from color 3D image data obtained from the surface scanner using a graphical user interface of the workstation;
   registering the robot arm to the surface scanner;
   calculating a robot movement quantity using a feedback control method according to a relative spatial relationship between the surgical path and the surgical tool, wherein the robot movement quantity comprises a translational component and a rotational component;
   repeating the previous step until an alignment error between the surgical tool and the surgical path is below a preset threshold, thereby aligning the surgical tool to the surgical path;
   moving the surgical tool with the robot arm in a position and direction corresponding to the surgical path using the robot movement quantity when the alignment error between the surgical tool and the surgical path is below the preset threshold, thereby performing the drilling operation.

2. The method of claim 1, wherein the robot movement quantity comprises a translation direction component ("$d_{robot}$") and a rotation component ("$r_{robot}$") of a tip of the surgical tool in the base coordinate frame of the robot arm ("$C_{robot}$"), wherein:

$$d_{robot} = (R_{robot}^{scan})^T e_{trans},$$

wherein $R_{robot}^{scan}$ is a rotation matrix from the coordinate frame of the surface scanner ("$C_{scan}$"), and $e_{trans}$ indicates a translational error quantity, and wherein:

$$r_{robot} = (R_{robot}^{scan})^T e_{rot},$$

wherein $e_{rot}$ indicates a rotational error quantity.

3. The method of claim 2, wherein the translational error quantity of the robot movement quantity is determined by the following formula:

$$e_{trans} = d_{tool}^{path} - (d_{tool}^{path} \cdot n_{scan}^{path}) n_{scan}^{path},$$

wherein $d_{tool}^{path}$ is a translational direction of the tip of the surgical tool in $C_{robot}$ and $n_{scan}^{path}$ is a translational direction of the surgical path in $C_{scan}$.

4. The method of claim 2, wherein the rotational error quantity of the robot movement quantity is determined by the following formula:

$$e_{rot} = \frac{r_{tool}^{path}}{\|r_{tool}^{path}\|} \cos^{-1}\left(\frac{n_{scan}^{path} \cdot n_{scan}^{tool}}{\|n_{scan}^{path}\| \|n_{scan}^{tool}\|}\right)$$

wherein $r_{tool}^{path}$ is a rotational component of the surgical path in in $C_{robot}$, $n_{scan}^{tool}$ is a translational direction of the tip of the surgical tool in $C_{scan}$, and $n_{scan}^{path}$ is a translational direction of the surgical path in $C_{scan}$.

5. The method of claim 1, wherein the 3D image data is acquired with a CT or MRI machine.

6. The method of claim 1, wherein the surface geometry data extracted from the 3D image data is selected from the group consisting of point clouds, triangular facets and meshes.

7. The method of claim 1, further comprising the step of preprocessing the surface geometry data, wherein preprocessing of the surface geometry data comprises the steps of down-sampling the data and removing a portion of the data corresponding to areas of the target surgery area which cannot be viewed from the surface scanner.

8. The method of claim 1, wherein a position and direction of the surgical path is continuously tracked by the surface scanner while aligning the surgical tool to the surgical path and moving the surgical tool with the robot arm in the position and direction corresponding to the surgical path.

9. The method of claim 8, further comprising the steps of:
   segmenting the surgical tool from the color 3D image data obtained from the scanner using binarization and morphologic operations;
   segmenting surface data corresponding to the segmented area of the previous step;
   registering the segmented surface data of the previous step to a CAD model of the surgical tool to acquire a transformation from the CAD model of the surgical tool to the surgical tool;
   calculating position and direction of the surgical tool with respect to the surface scanner.

10. The method of claim 1, wherein registering the robot arm to the surface scanner comprises the steps of:
   recording a first direction of the surgical tool tracked by the surface scanner and also calculating a direction of the surgical tool with respect to a base coordinate frame of a robot arm coordinate frame using kinematic data obtained from the robot arm;
   pointing the surgical tool to a second direction, recording the direction of the surgical tool tracked by the surface scanner and also calculating the direction of the surgical tool with respect to the base coordinate frame of the robot arm using the kinematic data obtained from the robot arm;

calculating the rotation matrix from the base coordinate frame of the robot arm to a coordinate frame of the surface scanner according to the directions in both coordinate frames acquired in the previous two steps using a singular value decomposition method.

11. The method of claim 10, wherein the singular value decomposition method is performed using the following singular value decomposition equation:

$$R_{robot}^{scan} = \underset{R \in Rotation\ matrix}{\operatorname{argmin}} \sum_{i=1,2} \|R(n_{robot}^{tool})_i - (n_{robot}^{tool})_i\|$$

wherein R is a rotation matrix, $R_{robot}^{scan}$ is the rotation matrix from a base coordinate frame of the robot arm to a coordinate frame of the surface scanning equipment, $n_{robot}^{tool}$ is a direction of the distal end of the surgical drill obtained using kinematic data obtained from the robot arm, and $n_{scan}^{tool}$ is a direction of the distal end of the surgical drill obtained from image data from the scanner.

* * * * *